United States Patent
Sallee et al.

(10) Patent No.: US 6,353,014 B1
(45) Date of Patent: Mar. 5, 2002

(54) 15-KETAL POSTAGLANDINS FOR THE TREATMENT OF GLAUCOMA OR OCULAR HYPERTENSION

(75) Inventors: Verney L. Sallee, Burleson; Mark R. Hellberg, Arlington; Peter G. Klimko, Fort Worth, all of TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/284,534

(22) PCT Filed: Nov. 7, 1997

(86) PCT No.: PCT/US97/20856

§ 371 Date: Jun. 2, 1999

§ 102(e) Date: Jun. 2, 1999

(87) PCT Pub. No.: WO98/20881

PCT Pub. Date: May 22, 1998

Related U.S. Application Data

(60) Provisional application No. 60/030,506, filed on Nov. 26, 1996.

(51) Int. Cl.[7] .......... A01N 43/38; A01N 43/90; A01N 43/42; A01N 43/18; A01N 43/12; A01N 43/16; A01N 43/08; A01N 43/26

(52) U.S. Cl. ............. 514/414; 514/305; 514/306; 514/307; 514/309; 514/310; 514/412; 514/416; 514/432; 514/443; 514/456; 514/461; 514/463; 514/464; 514/465; 514/467; 546/429; 546/134; 548/452; 548/469; 548/470; 548/482; 549/49; 549/51; 549/57; 549/78; 549/398; 549/399

(58) Field of Search ................ 514/307, 309, 514/306–310, 410, 412, 414, 416, 432, 443, 456, 401, 463–465, 467; 549/430, 448, 449, 49, 51, 57, 78, 398, 399, 401; 546/429, 134; 548/452, 469, 470, 482

(56) References Cited

U.S. PATENT DOCUMENTS

| | | | |
|---|---|---|---|
| 4,088,775 A | 5/1978 | Skuballa et al. | 424/278 |
| 4,870,104 A * | 9/1989 | Vorbrueggen et al. | 514/530 |
| 5,480,900 A | 1/1996 | DeSantis et al. | 514/392 |
| 5,587,391 A | 12/1996 | Burk | 514/357 |
| 5,605,922 A * | 2/1997 | DeSantis et al. | 514/392 |

FOREIGN PATENT DOCUMENTS

| | | | |
|---|---|---|---|
| CS | 242281 | * | 4/1986 |
| EP | 0 561 073 A1 | | 9/1993 |
| EP | 0 580 268 A2 | | 1/1994 |
| WO | WO 94/08585 | | 4/1994 |
| WO | WO 95/11682 | | 5/1995 |
| WO | WO 96/13267 | | 5/1996 |

OTHER PUBLICATIONS

Karlach et al, 15–glycal–cloprostenol and its metabolite 15–keto–cloprostenol on luteal tissue, Biopharm., (Jilove, Czech.), vol 2, 1–2, pp. 17–21, 1992.*

Kral et al, Stimulating progesterone secretion with some cloprostenol derivatives, Biol. Chem. Zivocisne Vyroby–Vet., vol 24, 3 pp. 207–14, 1988.*

Brambaifa, Luteolytic potency of 16–phenoxy–derivatives of PG F2. alpha., Experientia, vol. 44, 1, pp. 45–7, 1988.*

Vorbrueggen, PG analogs. 2. 15, 15–Ketals of natural PG's and PG analogs, J. Med. Chem, vol. 21, 5, pp. 443–7, 1978.*

Alm The Potential of Prostaglandin Derivatives in Glaucoma Therapy, *Current Opinion in Ophthalmology*, 4(11):44–50 (1993).

Brambaifa, Binding of a Novel Prostaglandin $F_{2\alpha}$–Derivative (ZK 71 677) To Pseudopregnant Rat Ovaries, *Journal Of Receptor Research* 6:(3&4):195–207 (1986).

Brambaifa, Luteolytic Potency of 16–Phenoxy–Derivatives of Prostaglandin $F_{2\alpha}$, *Experienta*, 44:45–47(1988).

Buhr et al, Luteolytic Potency in a Novel Prostaglandin Analogue, *Prostaglandins* 28(1):93–101 (Jul. 1984).

Giuffre, The Effects of Prostaglandin $F_{2\alpha}$ the Human Eye, *Graefe's Archive Ophthalmology* 222:139–141 (1985).

Kerstetter et al., Prostaglandin $F_{2\alpha}$–1–Isopropylester Lowers Intraocular Pressure Without Decreasing Aqueous Humor Flow, *American Journal of Ophthalmology* 105:30–34 (1988).

Nakajima et al, Effects of Prostaglandin $D_2$ and its Analogue, BW245C, on Intraocular Pressure in Human, *Graefe's Archive Ophthalmology*, 229:411–413 (1991).

Skuballa et al., 15,15–Ketals of Natural Prostaglandins and Prostaglandin Analogues Synthesis and Biological Activities, *J. Med. Chem* 21(5):443–447 (1978).

The Merck Index (Eleventh Ed.) Etiproston, p. 608, monograph No. 3827 (1989).

(List continued on next page.)

Primary Examiner—Alton Pryor
(74) Attorney, Agent, or Firm—Barry L. Copeland

(57) ABSTRACT

A method of treating glaucoma or ocular hypertension in a patient, which comprises administering to the patient a pharmaceutically effective amount of a compound of formula I:

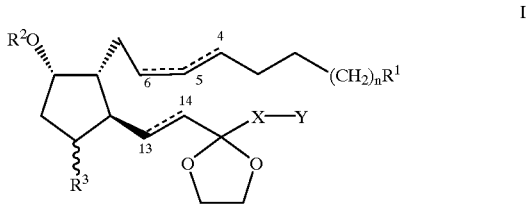

20 Claims, No Drawings

OTHER PUBLICATIONS

Woodward et al., Marked Differential Effects of Prostanoid Metabolite on Rabbit Intraocular Pressure, *Ophthalmic Res.* 21:428–435 (1989).

Woodward et al., Definition of Prostanoid Receptor Subtypes by Radioligand Binding and the Effects of Selective Agonists on Intraocular Pressure, *Exp. Eye Res.* 55(Suppl A): S.91 (1992).

Skuballa et al., "Prostanoic Acid Derivatives," *Chemical Abstract*, 85:20682 (1976).

* cited by examiner

15-KETAL POSTAGLANDINS FOR THE TREATMENT OF GLAUCOMA OR OCULAR HYPERTENSION

This application claims the benefit date of Provisional application No. 60/030,506 filed Nov. 26, 1996. This appln is a 371 of PCT/US97/20856 filed Nov. 7, 1997.

BACKGROUND OF THE INVENTION

The present invention relates to novel compounds and methods for the treatment of glaucoma and ocular hypertension. In particular, the present invention relates to the use of certain 15-ketal analogs of F series prostaglandins to treat glaucoma and ocular hypertension.

Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects, such as nausea, dyspepsia, fatigue, and metabolic acidosis, which side effects can affect patient compliance and/or necessitate the termination of treatment. Moreover, some beta-blockers have increasingly become associated with serious pulmonary side effects attributable to their effects on beta-2 receptors in pulmonary tissue. Sympathomimetics, on the other hand, may cause tachycardia, arrhythmia and hypertension. Recently, certain prostaglandins and prostaglandin derivatives have been described in the art as being useful in reducing intraocular pressure. Typically, however, prostaglandin therapy for the treatment of elevated intraocular pressure is attended by undesirable side-effects, such as irritation and hyperemia of varying severity and duration. There is therefore a continuing need for therapies which control the elevated intraocular pressure associated with glaucoma.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins are known in the art including A, B, C, D, E, F, G, I and J-Series prostaglandins (EP 0 561 073 A1). Of interest in the present invention are compounds which are believed to exhibit similar IOP lowering mechanisms to those exhibited by $PGF_{2\alpha}$, an F-series prostaglandin of the following formula:

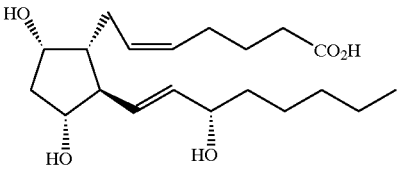

The relationship of $PGF_{2\alpha}$, receptor activation and IOP lowering effects is not well understood. It is believed that $PGF_{2\alpha}$ receptor activation leads to increased outflow of aqueous humor. Regardless of mechanism, $PGF_{2\alpha}$ and certain of its analogs have been shown to lower IOP (Giuffre, *The Effects of Prostaglandin $F_{2\alpha}$ the Human Eye, Graefe's Archive Ophthalmology*, volume 222, pages 139–141 (1985); and Kerstetter et al., *Prostaglandin $F_{2\alpha}$-1-Isopropylester Lowers Intraocular Pressure Without Decreasing Aqueous Humor Flow, American Journal of Ophthalmology*, volume 105, pages 30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (*Graefe's Archive Ophthalmology*, volume 229, pages 411–413 (1991)). Though $PGF_{2\alpha}$-type molecules lower IOP, these types of molecules have also been associated with undesirable side effects resulting from topical ophthalmic dosing. Such effects include an initial increase in IOP, breakdown of the blood aqueous barrier and conjunctival hyperemia (Alm, *The Potential of Prostaglandin Derivatives in Glaucoma Therapy, Current Opinion in Ophthalmology*, volume 4, No. 11, pages 44–50 (1993)). Based on the foregoing, a need exists for the development of compounds that may activate the $PGF_{2\alpha}$ receptors, yielding a more efficacious lowering of IOP, while exhibiting fewer or reduced side effects.

An agent which exhibits comparable efficacy, but with reduced side effects when compared to other agents, is said to have an improved therapeutic profile. It is an object of this invention to provide a class of IOP lowering agents with an improved therapeutic profile over $PGF_{2\alpha}$, and methods of their use. It has unexpectedly been found that the presently claimed 15-ketal analogs of $PGF_{2\alpha}$ meet this objective. Although etiproston, a 15-ketal prostaglandin and certain analogs thereof are known in the art (U.S. Pat. No. 4,088,775 and Skuballa, et al., "15-,15-ketals of Natural Prostaglandins and Prostaglandin Analogues Synthesis and Biological Activities," *J. Med. Chem*, 21(5):443 (1978)), they are known primarily for their luteolytic properties. See, e.g. *The Merck Index* (Eleventh Ed.) p. 608, monograph no. 3827 (1989). Etiproston was also disclosed in U.S. Pat. No. 5,480,900 as one of many prostaglandin analogs which in combination with a clonidine derivative would be useful for treating glaucoma. In addition, U.S. Pat. No. 4,870,104 discloses 11-halo prostaglandins which may have an ethylenedioxymethylene group at the 15 position. The novel compositions and the methods of use claimed in this application, however, are neither disclosed nor suggested in the foregoing art.

SUMMARY OF THE INVENTION

The present invention is directed to novel compounds, ophthalmic compositions and methods of their use in treating glaucoma and ocular hypertension. In particular, the present invention provides certain classes of 15-ketal prostaglandins believed to have functional $PGF_{2\alpha}$ receptor agonist activity, and methods of their use in treating glaucoma and ocular hypertension.

DETAILED DESCRIPTION OF THE INVENTION

It has unexpectedly been found that the 15-ketal substituted $PGF_{2\alpha}$ analogs of the present invention exhibit an improved therapeutic profile in the treatment of glaucoma and ocular hypertension when compared natural prostaglandins and some of their known analogs. The substituted $PGF_{2\alpha}$ analogs useful in the methods and compositions of the Ad present invention have the following formula I:

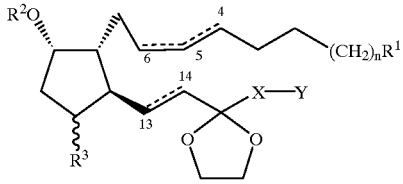

wherein:
$R^1$=$CO_2R$, $CONR^4R^5$, $CH_2OR^6$, or $CH_2NR^7R^8$, where:
R=H or cationic salt moiety, or $CO_2R$=pharmaceutically acceptable ester moiety; $R^4$, $R^5$=same or different=H or alkyl; $R^6$=H, acyl, or alkyl; $R^7$, $R^8$=same or different=H, acyl, or alkyl; with the proviso that if one of $R^7$, $R^8$=acyl, then the other=H or alkyl;

n=0 or 2;

$R^2$=H, alkyl, or acyl;

$R^3$=H, halo, or $OR^9$; where $R^9$=H, alkyl, or acyl;

- - - - =single or non-cumulated double bond, with the provisos that if a double bond is present between carbons 4 and 5, it is of the cis configuration; and that if a double bond is present between carbons 13 and 14, it is of the trans configuration;

X=$(CH_2)_m$ or $(CH_2)_mO$, where m=1–6; and

Y=phenyl, optionally substituted with alkyl, halo, trihalomethyl, alkoxy, acyl, acyloxy, amino, alkylamino, acylamino, or hydroxy; or X—Y=$(CH_2)_pY^1$; where p=0–6; and $Y^1$ = wherein:

W=$CH_2$, O, $S(O)_q$, $NR^{10}$, $CH_2CH_2$, CH=CH, $CH_2O$, $CH_2S(O)_q$, CH=N, or $CH_2NR^9$,
where q=0–2, and $R^{10}$=H, alkyl, or acyl;

Z=H, alkyl, alkoxy, acyl, acyloxy, halo, trihalomethyl, amino, alkylamino, acylamino, or hydroxy; and

- - - - =single or double bond.

For purposes of the foregoing and following definitions, the term "pharmaceutically acceptable ester" means any ester that would, in appropriate doses, be suitable for therapeutic administration to a patient by conventional means without significant deleterious health consequences; and "ophthalmically acceptable ester" means any pharmaceutically acceptable ester that would be suitable for ophthalmic application, i.e. non-toxic and non-irritating. Preferred are alkyl esters. Most preferred are $C_2$–$C_4$ alkyl esters, and especially isopropyl esters. In addition, references to "carbons 4 and 5", "carbons 5 and 6" and "carbons 13 and 14" shall mean the carbons so designated in the structural formulas even when n=2.

Preferred for use in the methods and compositions of the present invention are those compounds of formula I above, wherein:

$R^1$=$CO_2R$, where R=H; or $CO_2R$=ophthalmically acceptable ester moiety;

n=0;

$R^2$=H;

$R^3$=OH in the alpha (α) configuration, or Cl or F in the beta (β) configuration;

— — — =single or non-cumulated double bond, with the provisos that if double bond is present between carbons 4 and 5 or carbons 5 and 6, it is of the cis configuration; and that if a double bond is present between carbons 13 and 14, it is of the trans configuration;

X=$CH_2O$; and

Y=phenyl, optionally substituted with halo or trihalomethyl.

Especially preferred for use in the present invention are the following compounds:

| Compound Number | Compound Name | Compound Structure |
|---|---|---|
| II | (5Z,13E)-(9S,11R)-16-(3-Chlorophenoxy)-9,11-dihydroxy-15,15-(ethylenedioxy)-17,18,19,20-tetranor-5,13-prostadienoic acid isopropyl ester | 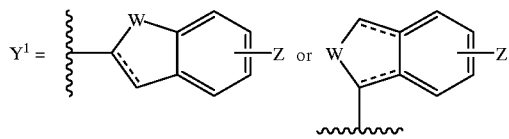 |

-continued

| Compound Number | Compound Name | Compound Structure |
|---|---|---|
| III | (5Z)-(9S,11R)-16-(3-Chlorophenoxy)-9,11-dihydroxy-15,15-(ethylenedioxy)-17,18,19,20-tetranor-5-prostenoic acid isopropyl ester | 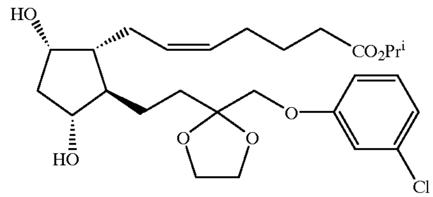 |
| IV | (4Z,13E)-(9S,11R)-16-(3-Chlorophenoxy)-9,11-dihydroxy-15,15-(ethylenedioxy)-17,18,19,20-tetranor-4,13-prostadienoic acid isopropyl ester | 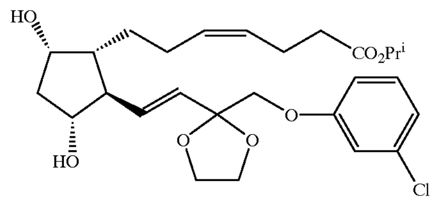 |
| V | (5Z,13E)-(9S,11S)-16-(3-Chlorophenoxy)-11-fluoro-9-hydroxy-15,15-(ethylenedioxy)-17,18,19,20-tetranor-5,13-prostadienoic acid isopropyl ester | 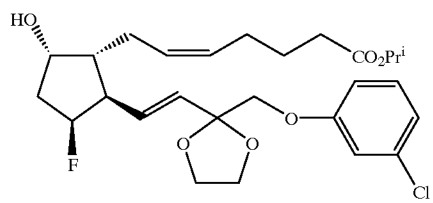 |
| VI | (5Z,13E)-(9S,11R)-9,11-Dihydroxy-15,15-(ethylenedioxy)-16-phenoxy-17,18,19,20-tetranor-5,13-prostadienoic acid isopropyl ester | 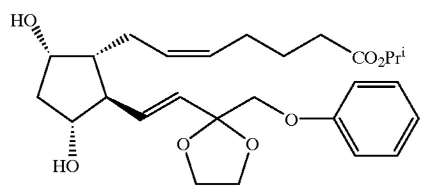 |
| VII | (5Z,13E)-(9S,11S)-11-Chloro-16-(3-chlorophenoxy)-15,15-(ethylenedioxy)-9-hydroxy-17,18,19,20-tetranor-5,13-prostadienoic acid isopropyl ester | 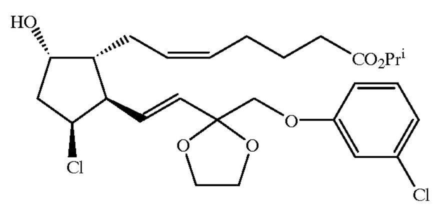 |

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis* by J. D. Morrison and J. W. Scott, Eds., Academic Press Publishers: New York, 1983–1985 (five volumes) and Principles of *Asymmetric Synthesis* by R. E. Gawley and J. Aube, Eds., Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*, G. Subramanian, Ed., VCH Publishers: New York, 1994; *Chiral Separations* by HPLC, A. M. Krstulovic, Ed., Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution or even mixing samples having different enantiomeric ratios.

The compounds of the present invention believed to be novel are the cis $\Delta^4$ compounds, i.e. those compounds of formula I, wherein:

$R^1$=$CO_2R$, $CONR^4R^5$, $CH_2OR^6$, or $CH_2NR^7R^8$; where:
  R=H or cationic salt moiety, or $CO_2R$= pharmaceutically acceptable ester moiety; $R^4$, $R^5$=same or different=H or alkyl; $R^6$=H, acyl, or alkyl; $R^7$, $R^8$=same or different=H, acyl, or alkyl; with the proviso that if one of $R^7$, $R^8$=acyl, then the other=H or alkyl;

n=0 or 2;

$R^2$=H, alkyl, or acyl;

$R^3$=H, halo, or $OR^9$; where $R^9$=H, alkyl, or acyl;

- - - - =single or non-cumulated double bond, with the provisos that a cis double bond is present between carbons 4 and 5; and that if a double bond is present between carbons 13 and 14, it is of the trans configuration;

$X=(CH_2)_m$ or $(CH_2)_mO$, where m=1–6; and

Y=phenyl, optionally substituted with alkyl, halo, trihalomethyl, alkoxy, acyl, acyloxy, amino, alkylamino, acylamino, or hydroxy; or X—Y=$(CH_2)_pY^1$; where p=0–6; and

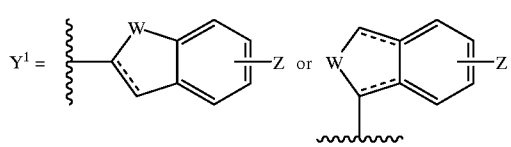

wherein:
W=$CH_2$, O, $S(O)_q$, $NR^{10}$, $CH_2CH_2$, CH=CH, $CH_2O$, $CH_2S(O)_q$, CH=N, or $CH_2NR^9$,
where q=0–2, and $R^{10}$=H, alkyl, or acyl;

Z=H, alkyl, alkoxy, acyl, acyloxy, halo, trihalomethyl, amino, alkylamino, acylamino, or hydroxy; and

- - - - =single or double bond.

Preferred novel compounds are those of formula I, wherein:

$R^1$=$CO_2R$; where R=H; or $CO_2R$=pharmaceutically acceptable ester moiety;

n=0;

$R^2$=H;

$R^3$=OH in the alpha (α) configuration, or Cl or F in the beta (β) configuration;

- - - - =single or non-cumulated double bond, with the provisos that a cis double bond is present between carbons 4 and 5 and that if a double bond is present between carbons 13 and 14, it is of the trans configuration;

X=$CH_2O$; and

Y=phenyl, optionally substituted with halo, or trihalomethyl.

Other related PGFs within the scope of the present invention are known and their syntheses are either described in the literature or can be achieved by methods similar to those described in the literature or otherwise known to those of skill in the art (eg. Skuballa et. al. U.S. Pat. No. 4,088,775; Vorbruggen et. al. U.S. Pat. No. 4,870,104). The foregoing references are by this reference incorporated herein.

In the foregoing illustrations, as well as those provided hereinafter, wavy line attachments indicate either the alpha (α) or beta (β) configuration. The carbon numbering is as indicated in structural formula I, even when n=2. A hatched line, as used e.g. at carbon 9, indicates the α configuration. A solid triangular line indicates the β configuration. Dashed lines on bonds, e.g. between carbons 5 and 6, indicate a single or double bond. Two solid lines between carbons indicate a double bond of the specified configuration.

In the following Examples 1–6, the following standard abbreviations are used: g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

Preparation of II

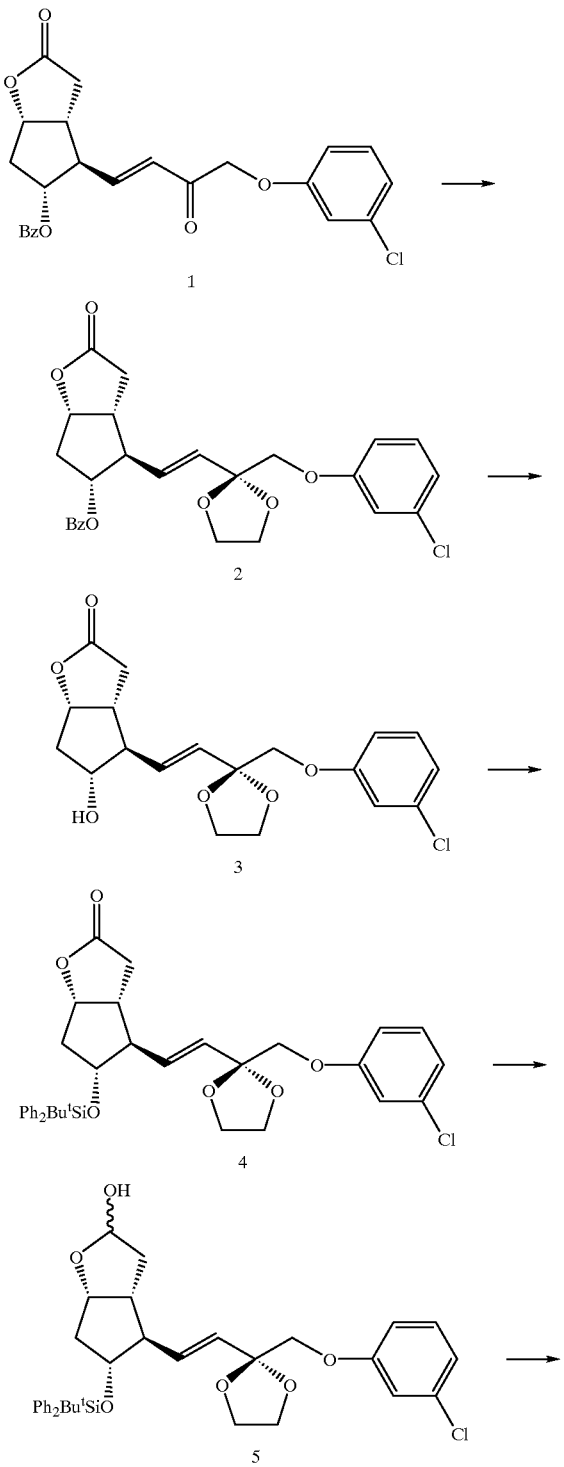

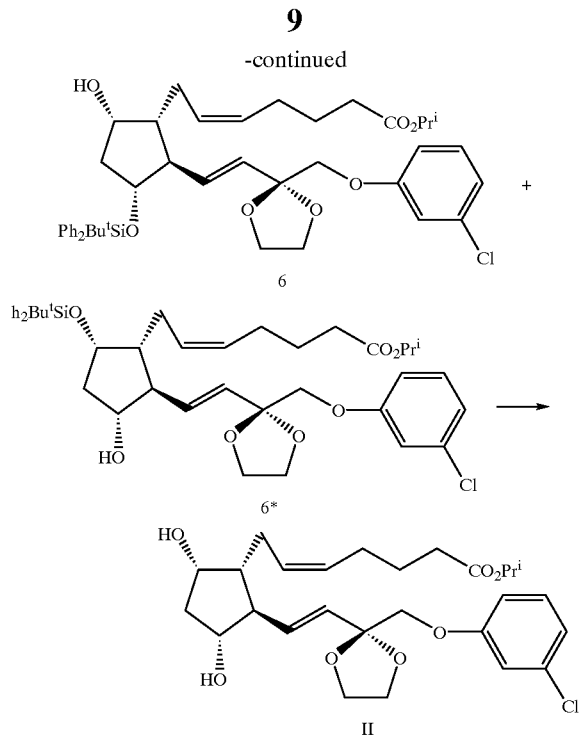

A. [3aR,4R(1E),5R,6aS]-5-(Benzoyloxy)-4-[4-(3-chlorophenoxy)-3,3-(ethylenedioxy)butenyl]-hexahydro-2H-cyclopenta[b]furan-2-one (2)

To a solution of [3aR,4R(1E),5R,6aS)-5-(benzoyloxy)-4-[4-(3-chlorophenoxy)-3-oxobutenyl]-hexahydro-2H-cyclopenta[b]furan-2-one (1; for preparation see published European Patent Application No. EP 639563 A2, which is incorporated by this reference) (1.32 g, 3.0 mmol), 4A molecular sieves (1.27 g), and 1,2-bis(trimethylsiloxy)ethane (1.27 g, 6.18 mmol) in methylene chloride (23 mL) at −78° C. (bath temperature) was added trimethylsilyl trifluoromethanesulfonate (172 mg, 0.77 mmol). The reaction was then warmed to −20 ° C. and maintained at that temperature overnight. Triethylamine (0.8 mL) was added, the solution was warmed to room temperature, saturated sodium bicarbonate (15 mL) was added, the layers were separated, the aqueous phase was extracted with methylene chloride (2×20 mL), the combined organic layers were dried (magnesium sulfate), filtered, concentrated, and chromatographed on a 19 cm tall×26 mm diameter silica gel column eluting with 1:1 ethyl acetate:hexane to afford 2 (1.41 g, 97%) $^{13}$C NMR (CDCl$_3$) δ176.17 (C), 165.92 (C), 159.23 (C), 134.71 (C), 133.32 (CH), 131.06 (CH), 130.06 (CH), 129.56 (CH), 129.40 (CH), 128.48 (CH), 121.37 (CH), 115.14 (CH), 113.21 (CH), 106.27 (C), 83.10 (CH), 78.76 (CH), 71.36 (CH$_2$), 65.41 (CH$_2$), 65.23 (CH$_2$), 53.74 (CH), 42.47 (CH), 37.35 (CH$_2$), 34.79 (CH$_2$).

B. [3aR,4R(1E),5R,6aS]-4-[4-(3-chlorophenoxy)-3,3-(ethylenedioxy)butenyl]-5-hexahydro-2H-cyclopenta[b]furan-2-one (3)

To a solution of 2 (1.64 g, 3.38 mmol) in methanol (25 mL) was added potassium carbonate (480 mg, 3.47 mmol). After 18 h, saturated ammonium chloride (45 mL) was added, the mixture was extracted with ethyl acetate (3×30 mL), dried (magnesium sulfate), filtered, and chromatographed on a 20 cm tall×26 mm diameter silica gel column eluting with 1:1 ethyl acetate:hexane to afford 3 (201 mg, 16%).

C. [3aR,4R(1E),5R,6aS]-5-(t-Butyldiphenylsiloxy)-4-[4-(3-chlorophenoxy)-3,3-(ethylenedioxy)butenyl]-hexahydro-2H-cyclopenta[b]furan-2-one (4)

To a solution of 3 (200 mg, 0.52 mmol), imidazole (125 mg, 1.84 mmol) and 4-(dimethylamino)pyridine (DMAP) (28 mg, 0.23 mmol) in methylene chloride (4 mL) was added t-butyldiphenylsilyl chloride (200 mg, 0.73 mmol). After 40, min saturated ammonium chloride (15 mL) was added, the solution was extracted with methylene chloride (3×15 mL), dried (magnesium sulfate), filtered, concentrated, and chromatographed on a 14 cm tall×26 mm diameter silica gel column eluting with 40% ethyl acetate in hexane to afford 4 (316 mg, 98%).

D. [3aR,4R(1E),5R,6aS]-5-(t-Butyldiphenylsiloxy)-4-[4-(3-chlorophenoxy)-3,3-(ethylenedioxy)butenyl]-hexahydro-2H-cyclopenta[b]furan-2-ol (5)

To a solution of 4 (310 mg, 0.50 mmol) in toluene (7 mL) at −78° C. (bath temperature) was added a 1.5 M solution of diisobutylaluminum hydride (DIBAL-H) in toluene (0.46 mL, 0.69 mmol). After 1 h, a 1:1 v:v solution of ethyl acetate:methanol (4 mL) was added, the solution was warmed to room temperature, saturated ammonium chloride (30 mL) and ethyl acetate (30 mL) were added, the thick mixture was filtered through Celite, the phases were separated, the aqueous layer was extracted with ethyl acetate (2×30 mL), the combined organic layers were dried (magnesium sulfate), filtered, and concentrated to afford crude 5 (320 mg, 100%), which was used directly in the next step without further purification.

E. (5Z, 13E)-(9S,11R)-11-(t-Butyldiphenylsiloxy)-16-(3-chlorophenoxy)-15,15-(ethylenedioxy)-9-hydroxy-17,18,19,20-tetranor-5,13-prostadienoic acid isopropyl ester (6)

To a suspension of (4-carboxybutyl)triphenylphosphonium bromide (685 mg, 1.55 mmol) in THF (7 mL) at 0° C. (bath temperature) was added a 1 M solution of potassium t-butoxide in THF (3.1 mL, 3.1 mmol). After 12 min, 5 (320 mg, 0.5 mmol) was added as a solution in THF (7 mL); and after 40 min, additional portions of (4-carboxybutyl)triphenylphosphonium bromide (700 mg, 1.58 mmol) and potassium t-butoxide (6 mL, 6 mmol) were added. After an additional 45 min, saturated ammonium chloride (20 mL) was added, the solution extracted with ethyl acetate (3×25 mL), dried (magnesium sulfate), filtered, and concentrated to afford an oil. To a solution of this oil, DMAP(45 mg, 0.37 mmol), isopropanol (1.0 g, 16.7 mmol), and 4A molecular sieves (300 mg) in methylene chloride (6.5 mL) was added 1-(3-dimethylaminopropyl)-3-ethylcarbodiimide hydrochloride (320 mg, 1.67 mmol). After 18 h, saturated ammonium chloride (25 mL) was added, the layers were separated, the aqueous phase was extracted with methylene chloride (2×20 mL), the combined organic layers were dried (magnesium sulfate), filtered, and chromatographed on a 17 cm tall×26 mm diameter silica gel column eluting with 30% ethyl acetate in hexane to afford 6 and the chromatographically separable siloxy transposition isomer 6* (121 mg combined, 32%).

F. (5Z,13E)-(9S,11R)-16-(3-Chlorophenoxy)-9,11-dihydroxy-15,15-(ethylenedioxy)-17,18,19,20-tetranor-5,13-prostadienoic acid isopropyl ester (II)

To a solution of a mixture of 6 and 6* (34 mg, 0.045 mmol) in THF (3 mL) was added a 1 M solution of tetrabutylammonium fluoride (TBAF) in THF (0.2 mL, 0.2 mmol). After 1 h, saturated ammonium chloride (3 mL) was added, the solution was extracted with ethyl acetate (4×3 mL), concentrated, and chromatographed on a 19 cm tall×10 mm diameter silica gel column eluting with 9:1 ethyl acetate:hexane to afford II (18.2 mg, 79%). $^{13}$C NMR (CDCl$_3$) d 173.39 (C), 159.45 (C), 134.76 (C), 134.68 (CH), 130.14 (CH), 129.88 (CH), 128.89 (CH), 128.11 (CH), 121.28 (CH), 115.29 (CH), 113.30 (CH), 106.62 (C), 78.31 (CH), 73.36 (CH), 71.47 (CH$_2$), 67.63 (CH), 65.34 (CH$_2$), 65.32 (CH$_2$), 55.76 (CH), 50.74 (CH), 42.89 (CH$_2$), 33.99 (CH$_2$), 26.61 (CH$_2$), 25.82 (CH$_2$O, 24.84 (CH$_2$), 21.83 (CH$_3$). MS, m/z calcd. for C$_{27}$H$_{37}$O$_7$ClNa [(M+Na)$^+$], 531; found 531.

EXAMPLE 2

Preparation of III

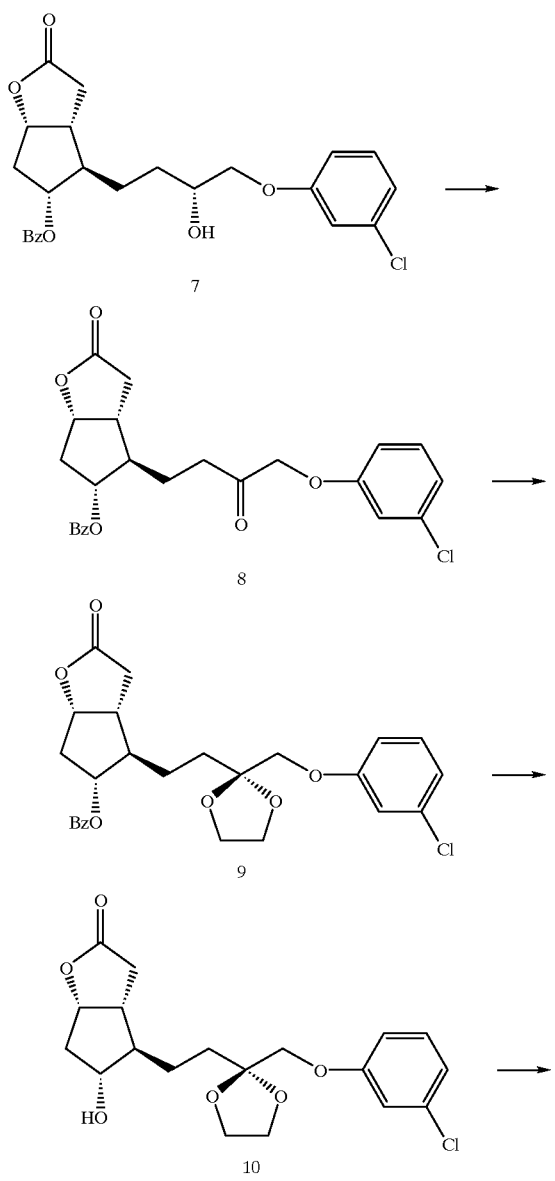

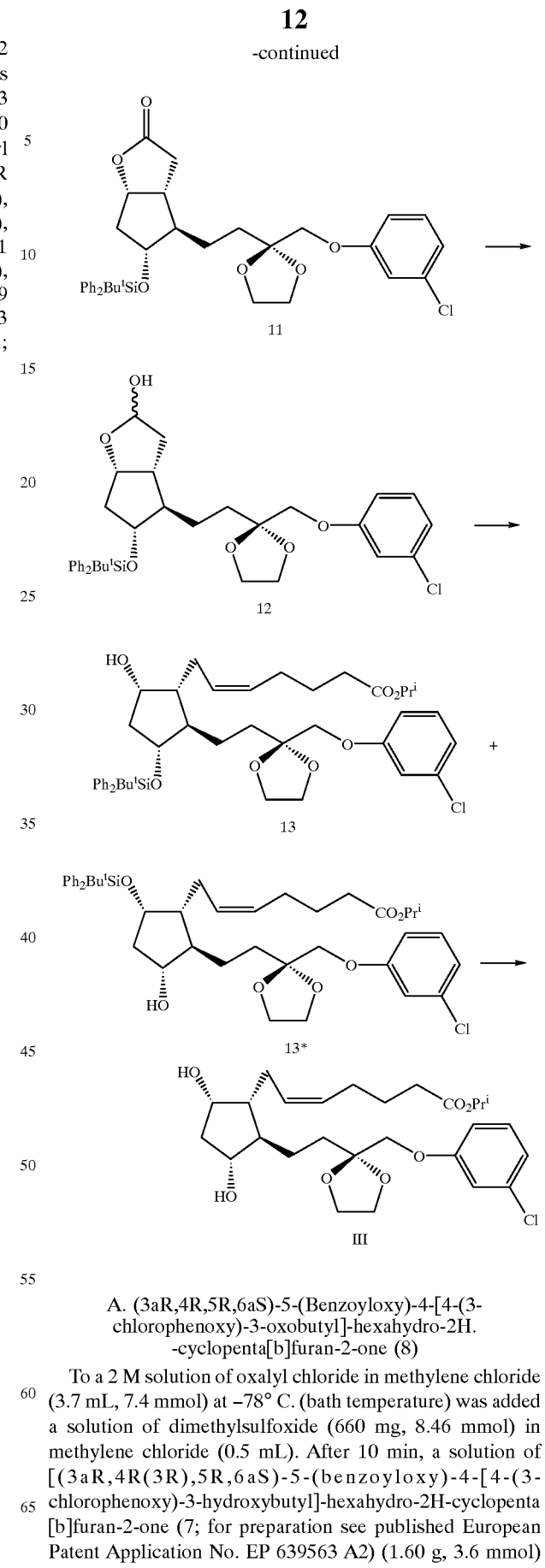

A. (3aR,4R,5R,6aS)-5-(Benzoyloxy)-4-[4-(3-chlorophenoxy)-3-oxobutyl]-hexahydro-2H.-cyclopenta[b]furan-2-one (8)

To a 2 M solution of oxalyl chloride in methylene chloride (3.7 mL, 7.4 mmol) at −78° C. (bath temperature) was added a solution of dimethylsulfoxide (660 mg, 8.46 mmol) in methylene chloride (0.5 mL). After 10 min, a solution of [(3aR,4R(3R),5R,6aS)-5-(benzoyloxy)-4-[4-(3-chlorophenoxy)-3-hydroxybutyl]-hexahydro-2H-cyclopenta[b]furan-2-one (7; for preparation see published European Patent Application No. EP 639563 A2) (1.60 g, 3.6 mmol)

in methylene chloride (25 mL) was added dropwise. After an additional 2 h, triethylamine (1.31 g, 12.9 mmol) was added, the reaction was warmed to room temperature, saturated ammonium chloride (50 mL) was added, the solution was extracted with methylene chloride (3×40 mL), dried (magnesium sulfate), filtered, concentrated, and chromatographed on a 16 cm tall×41 mm diameter silica gel column eluting with 1:1 ethyl acetate:hexane to afford 8 (1.17 g, 73%).

B. (3aR,4R,5R,6aS)-5-(Benzoyloxy)-4-[4-(3-chlorophenoxy)-3,3-(ethylenedioxy)butyl]-hexahydro-2H-cyclopenta[b]furan-2-one (9)

To a solution of 8 (1.29 g, 2.91 mmol), 4A molecular sieves (1.7 g) and 1,2-bis(trimethylsiloxy)ethane (1.2 g, 5.8 mmol) in methylene chloride (20 mL) at 0° C. (bath temperature) was added trimethylsilyl trifluoromethanesulfonate (170 mg, 0.76 mmol). After 2 h, the reaction was warmed to room temperature, cooled to 4° C. (bath temperature) and maintained at that temperature over 72 h. Triethylamine (1 mL) and saturated sodium bicarbonate (20 mL) were added sequentially, the solution was extracted with ethyl acetate (3×35 mL), dried (magnesium sulfate), filtered, concentrated, and chromatographed on a 17 cm tall×26 mm diameter silica gel column eluting with 1:1 ethyl acetate:hexane to afford 9 (1.20 g, 84%). $^{13}$C NMR (CDCl$_3$) δ176.75 (C), 166.00 (C), 159.22 (C), 134.87 (C), 133.22 (CH), 130.23 (CH), 129.65 (CH), 129.61 (CH), 128.48 (CH), 121.42 (CH), 115.04 (CH), 113.12 (CH), 108.78 (C), 84.41 (CH), 80.26 (CH), 70.15 (CH$_2$), 65.67 (CH$_2$), 65.62 (CH$_2$), 52.70 (CH), 43.40 (CH), 37.61 (CH$_2$), 36.27 (CH$_2$), 33.00 (CH$_2$), 26.60 (CH$_2$).

C. (3aR,4R,5R,6aS)-4-[4-(3-chlorophenoxy)-3,3-(ethylenedioxy)butyl]-5-hydroxy-hexahydro-2H-cyclopenta[b]furan-2-one (10)

To a solution of 9 (1.15 g, 2.36 mmol) in methanol (40 mL) was added potassium carbonate (389 mg, 2.81 mmol). After 3.5 h, saturated ammonium chloride (45 mL) and saturated brine (25 mL) were added, the mixture was extracted with ethyl acetate (3×60 mL), dried (magnesium sulfate), filtered, concentrated, and chromatographed on a 14 cm tall×41 mm diameter silica gel column eluting with 4:1 ethyl acetate:hexane to afford 10 (708 mg,81%).

D. (3aR,4R,5R,6aS)-5-(t-Butyldiphenylsiloxy)-4-[4-(3-chlorophenoxy)-3,3-(ethylenedioxy)butyl]-hexahydro-2H-cyclopenta[b]furan-2-one (11)

To a solution of 10 (700 mg, 1.89 mmol), DMAP (58 mg, 0.48 mmol), and imidazole (192 mg, 2.82 mmol) in methylene chloride (11 mL) was added t-butyldiphenylsilyl chloride (670 mg, 2.45 mmol). After 4.5 h, saturated ammonium chloride (15 mL) was added, the phases were separated, the aqueous layer was extracted with methylene chloride (2×15 mL), the combined organic layers were dried (magnesium sulfate), filtered, concentrated, and chromatographed on a 22 cm tall×26 mm diameter silica gel column eluting with 40% ethyl acetate in hexane to afford 11 (951 mg, 83%).

E. (3aR,4R,5R,6aS)-5-(t-Butyldiphenylsiloxy)-4-[4-(3-chlorophenoxy)-3,3-(ethylenedioxy)butyl]-hexahydro-2H-cyclopenta[b]furan-2-ol (12)

To a solution of 11 (945 mg, 1.55 mmol) in toluene (11 mL) at −78° C. (bath temperature) was added a 1.5 M solution of DIBAL-H in toluene (3.0 mL, 4.5 mmol). After 3.5 h, ethyl acetate (10 mL) was added, the mixture was warmed to room temperature, saturated sodium potassium tartrate (20 mL) was added, and the thick solution was stirred for 30 min to break the emulsion. The layers were separated, the aqueous phase was extracted with ethyl acetate (2×30 mL), the combined organic layers were dried (magnesium sulfate), filtered, concentrated, and chromatographed on a 13 cm tall×26 mm diameter silica gel column eluting with 40% ethyl acetate in hexane to afford 12 (968 mg, 100%).

F. (5Z)-(9S,11R)-11-(t-Butyldiphenylsiloxy)-16-(3-chlorophenoxy)-15,15-(ethylenedioxy)-9-hydroxy-17,18,19,20-tetranor-5-prostenoic acid isopropyl ester (13)

To a suspension of (4-carboxybutyl)triphenylphosphonium bromide (2.1 g, 4.7 mmol) in THF (22 mL) at 0° C. (bath temperature) was added a 1 M solution of potassium t-butoxide in THF (9.4 mL, 9.4 mmol). After 15 min, a solution of 12 (960 mg, 1.57 mmol) in THF (13 mL) was added dropwise. After an additional 4 h, saturated ammonium chloride (30 mL) was added, the mixture was extracted with ethyl acetate (3×30 mL), dried (magnesium sulfate), filtered, and concentrated to afford a crude oil. This oil was dissolved in acetone (15 mL), the bath temperature was lowered to 0° C., and DBU (1.4 g, 9.2 mmol) was added. After 20 min, isopropyl iodide (1.6 g, 9.4 mmol) was added, and the mixture was warmed to room temperature and stirred over 3 d. Saturated ammonium chloride (25 mL) was added, the mixture was extracted with ethyl acetate (3×25 mL), dried (magnesium sulfate), filtered, concentrated, and chromatographed on a 17 cm tall×26 mm diameter silica gel column eluting with 30% ethyl acetate in hexane to afford 13 and the siloxy transposition isomer 13* (791 mg combined, 67%).

G. (5Z)-(9S,11R)-16-(3-Chlorophenoxy)-9,11-dihydroxy-15,15-(ethylenedioxy)-17,18,19,20-tetranor-5-prostenoic acid isopropyl ester (III)

To a solution of the above mixture of 13 and 13* (785 mg, 1.05 mmol) in THF (10 mL) was added a 1 M solution of TBAF in THF (3 mL, 3 mmol). After 1 h, saturated ammonium chloride (40 mL) was added, the mixture was extracted with ethyl acetate (3× 30 mL), dried (magnesium sulfate), filtered, concentrated, and chromatographed on a 22 cm tall×26 mm diameter silica gel column eluting with 1:1 ethyl acetate:hexane to afford III (392 mg, 73%). $^{13}$C NMR (CDCl$_3$) δ173.36 (C), 159.37 (C), 134.81 (C), 130.18 (CH), 129.66 (CH), 129.22 (CH), 121.28 (CH), 115.07 (CH), 113.63 (CH), 109.17 (C), 78.65 (CH), 74.72 (CH), 70.29 (CH$_2$), 67.57 (CH), 65.67 (CH$_2$), 65.56 (CH$_2$), 52.93 (CH), 51.79 (CH), 42.43 (CH$_2$), 34.04 (CH$_2$), 33.58 (CH$_2$), 26.93 (CH$_2$), 26.88 (CH$_2$), 26.64 (CH$_2$),24.90 (CH$_2$), 21.82 (CH$_3$). MS, m/z calcd. for C$_{27}$H$_{39}$O$_7$ClNa [(M+Na)$^+$], 533; found, 533.

EXAMPLE 3

Synthesis of IV

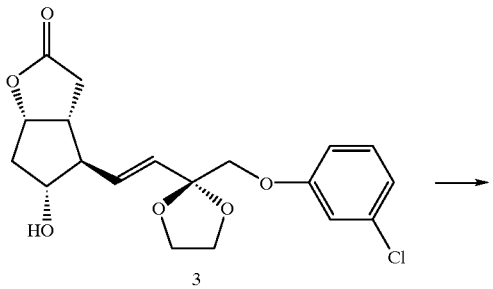
3

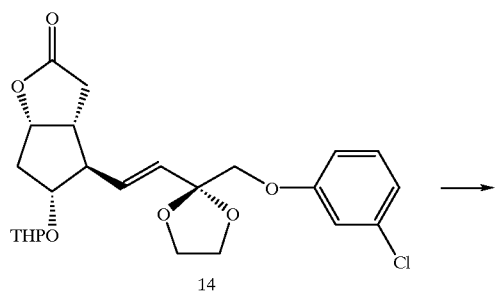
14

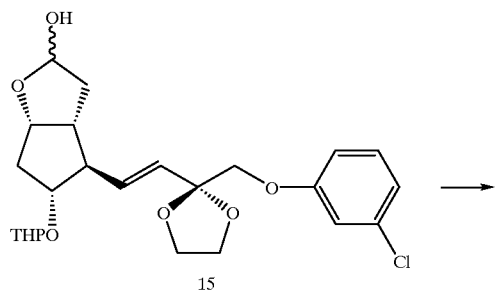
15

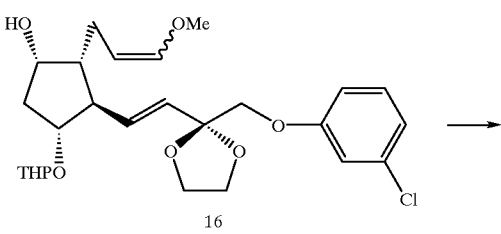
16

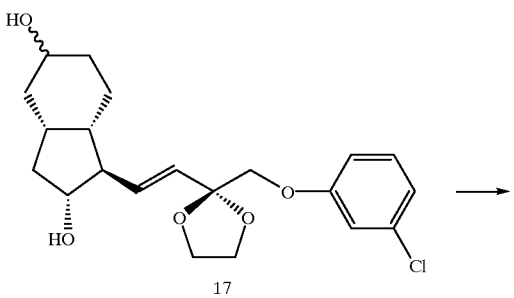
17

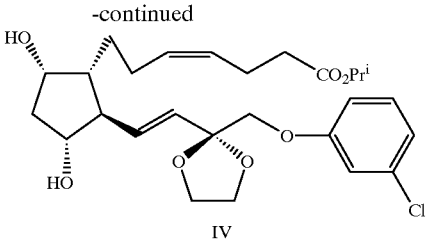
IV

(4Z,13E)-(9S,11R)-1 6-(3-Chlorophenoxy)-9,11-dihydroxy-15,15-(ethylenedioxy)-17,18,19,20-tetranor-4,13-prostadienoic acid isopropyl ester (IV)

Reaction of alcohol 3 with 3,4-dihydro-2H-pyran in $CH_2Cl_2$ at 0° C. in the presence of p-toluenesulfonic acid affords 14, reduction of which with DIBAL-H in toluene at −78° C. provides lactol 15. Wittig reaction of lactol 15 with $Ph_3P^+CH_2OMe$ $Cl^-$ in the the presence of potassium t-butoxide in THF affords enol ether 16 as a mixture of enol ether olefin geometrical isomers. Treatment of this mixture with p-toluenesulfonic acid in THF/water affords lactol 17. Wittig reaction of 17 with $Ph_3P^+(CH_2)_3CO_2H$ $Br^-$ in the presence of potassium t-butoxide in THF, followed by treatment of an acetone solution of the resulting carboxylic acid with DBU and isopropyl iodide, yields IV after purification via silica gel chromatography.

EXAMPLE 4

Synthesis of V

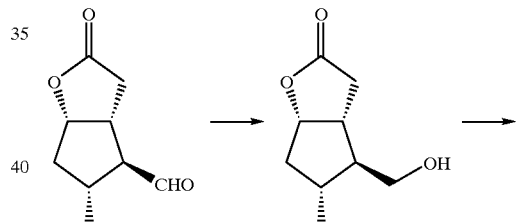
18   19

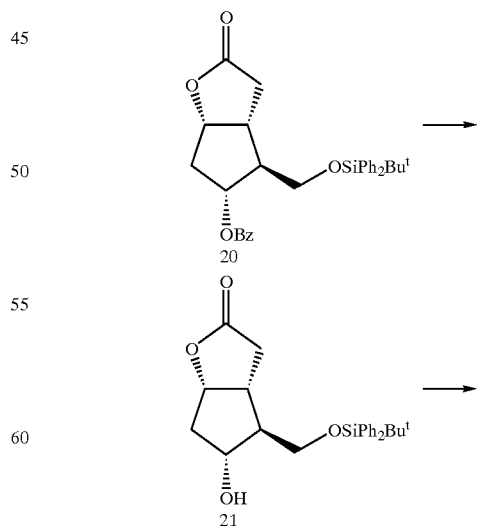
20

21

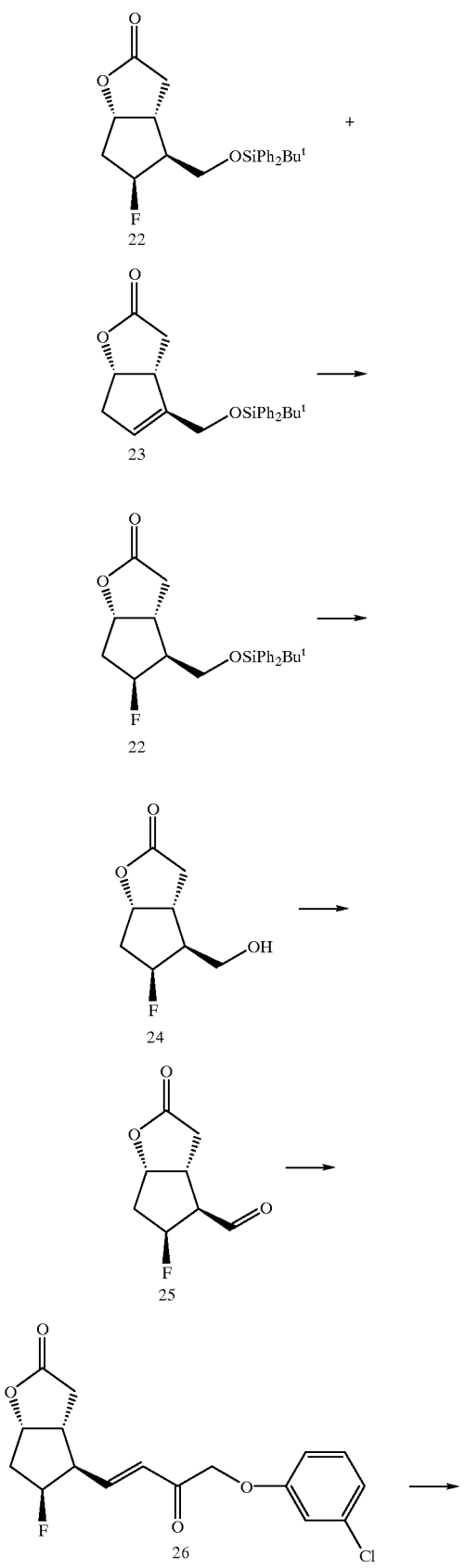

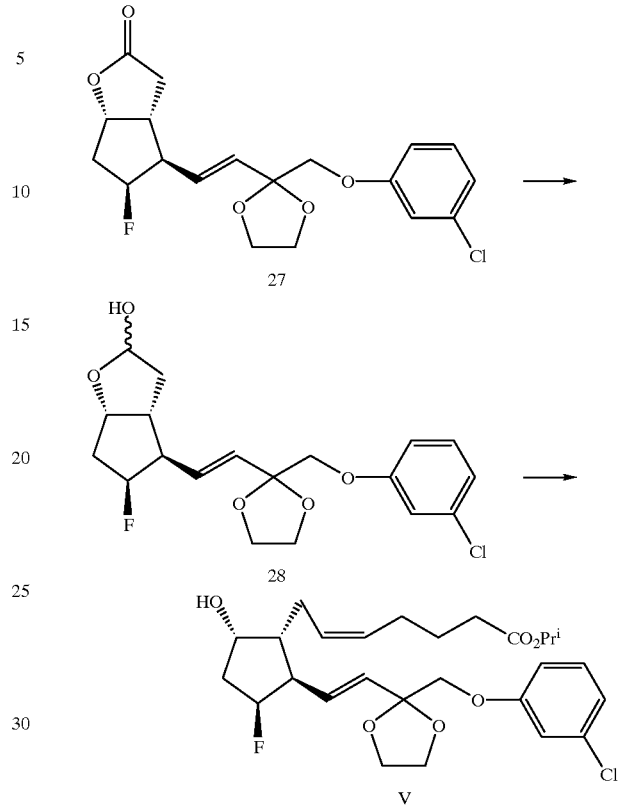

(5Z,13E)-(9S,11S)-16-(3-Chlorophenoxy)-11-fluoro-9-hydroxy-15,15-(ethylenedioxy)-17,18,19,20-tetranor-5,13-prostadienoic acid isopropyl ester (V)

Reduction of aldehyde 18 to alcohol 19 is accomplished using NaBH$_4$ in a 1:1 mixture of CH$_2$Cl$_2$:MeOH. Silylation to 20 is accomplished via treatment with Ph$_2$Bu$^t$SiCl, imidazole, 4-(dimethylamino)pyridine in CH$_2$Cl$_2$. Debenzoylation is effected with K$_2$CO$_3$ in MeOH to provide 21. Fluorination with (diethylamino)sulfur trifluoride in CH$_2$Cl$_2$ at 0° C. affords a mixture of 22 and an elimination by-product 23. This mixture is treated with OsO$_4$ and 4-methylmorpholine N-oxide in acetone/water to afford a now easily chromatographically separable mixture of 22 and a dihydroxylation product of 23. Desilylation of 22 with TBAF in THF yields alcohol 24, which is oxidized to aldehyde 25 using Swern conditions (oxalyl chloride/DMSO). Horner-Emmons reaction of 25 with dimethyl [3-(3-chlorophenoxy)-2-oxopropyl]phosphonate in THF in the presence of NEt$_3$/LiCl affords enone 26. Ketalization is achieved by treatment with 1,2-bis(trimethylsiloxy)ethane and trimethylsilyl trifluoromethanesulfonate in CH$_2$Cl$_2$ from −78° C. to −20° C. overnight to give 27. Reduction of 27 with 1 equivalent of DIBAL-H in toluene at −78° C. provides lactol 28. Wittig reaction with Ph$_3$P$^+$(CH$_2$)$_4$CO$_2$H Br$^-$ in THF in the presence of potassium t-butoxide, followed by esterification of an acetone solution of the resulting acid with isopropyl iodide/DBU, affords V after purification via silica gel chromatography.

EXAMPLE 5

Synthesis of VI

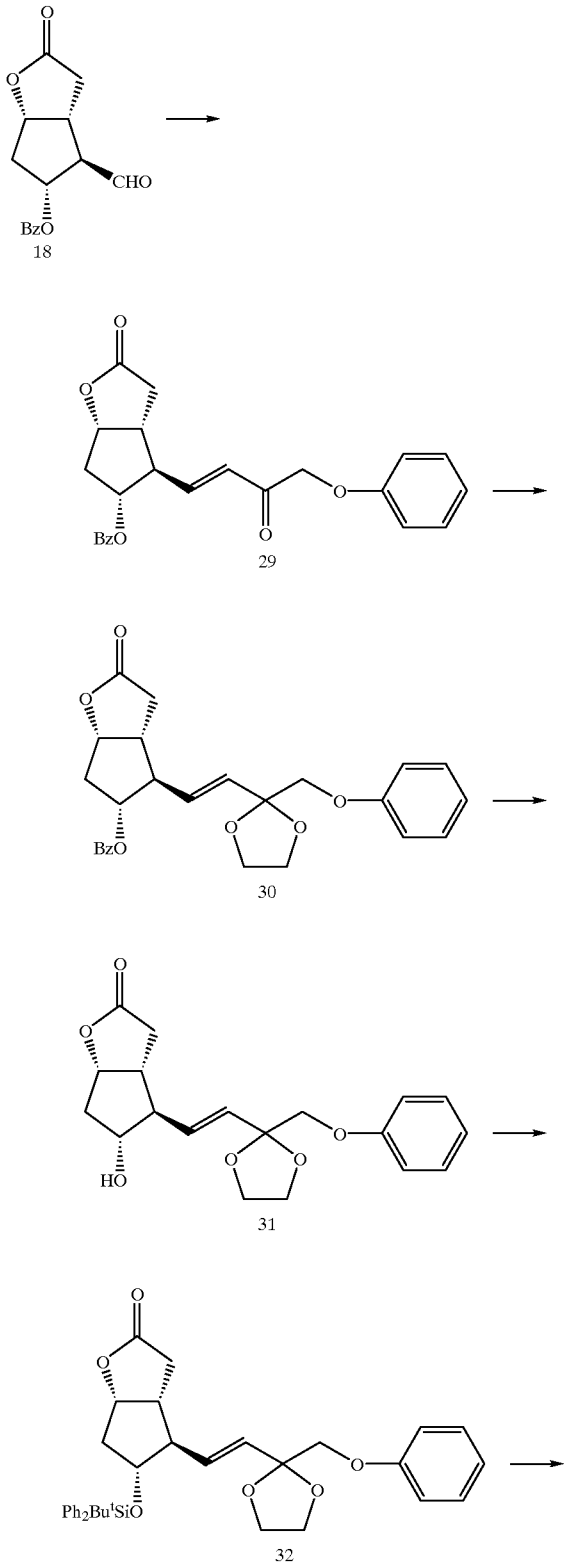

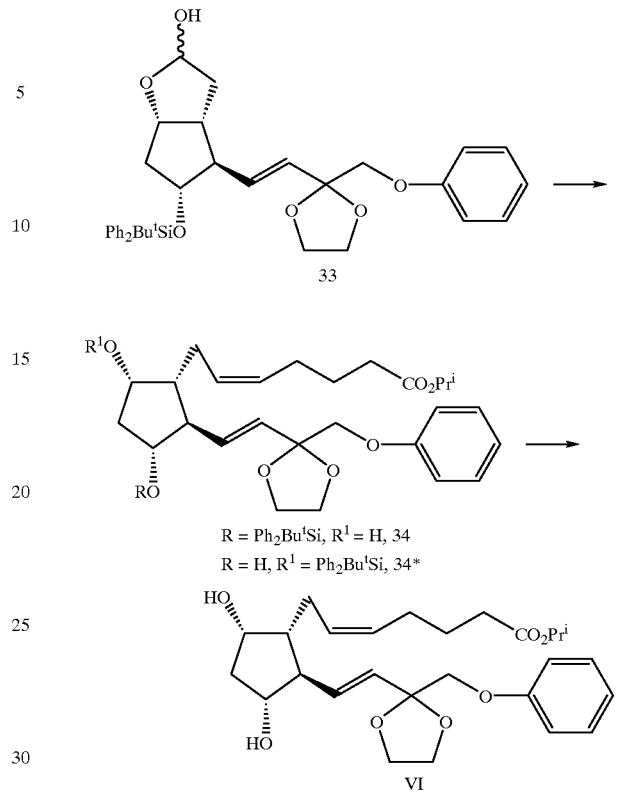

A. [3aR,4R(1E),5R,6aS]4-(Benzoyloxy)-4-(4-phenoxy-3-oxobutyl)-hexahydro-2H-cyclopenta[b]furan-2-one (29)

To a solution of lithium chloride (920 mg, 22 mmol) and dimethyl (2-oxo-3-phenoxypropyl)phosphonate (prepared in a manner analogous to that described in U.S. Pat. No. 5,665,773 for dimethyl (2-oxo-3-(3-chlorophenoxy)propyl) phosphonate, which patent is incorporated herein by this reference) (3.50 g, 13.6 mmol) in THF (30 mL) at 0° C. (bath temperature) was added NEt$_3$ (1.20 g, 11.9 mmol). After 10 min, aldehyde 18 was added in one portion to the suspension. After 2 h, the suspension was added to saturated NH$_4$Cl (30 mL), the mixture was extracted with ethyl acetate (3×30 mL), dried (MgSO$_4$), filtered, concentrated, and chromatographed on a 15 cm tall×41 mm diameter silica gel column eluting with 1:1 ethyl acetate:hexane to afford 29 (1.30 g, 40 %).

B. [3aR,4R(1E),5R,6aS]-(Benzoyloxy)-4-[4-(3-chlorophenoxy)-3,3-(ethylenedioxy)butenyl]-]-hexahydro-2H-cyclopenta[b]furan-2-one (30)

To a solution of enone 29 (1.30 g, 3.2 mmol) and 1,2-bis(trimethylsiloxy)ethane (1.34 g, 6.5 mmol) in CH$_2$Cl$_2$ (10 mL) at −78° C. (bath temperature) was added trimethylsilyl trifluoromethanesulfonate (240 mg, 1.1 mmol). After 1 h, the reaction was warmed to −20° C. and kept at that temperature overnight. The reaction was quenched by the addition of NEt₃ (360 mg, 3.56 mmol), warmed to room temperature, added to saturated sodium bicarbonate (25 mL), the layers were separated, the aqueous layer was extracted with CH₂Cl₂ (3×25 mL), ), dried (MgSO₄), filtered, concentrated, and chromatographed on a 12 cm tall×41 mm diameter silica gel column to afford 30 (1.19 g, 82%).

C. [3aR,4R(E),5,R6aS]-5-Hydroxy-4-[4-(3-chlorophenoxy)-3,3-(ethylenedioxy)butenyl]-hexahydro-2H-cyclopenta[b]furan-2-one (31)

To a solution of 30 (1.18 g, 2.62 mmol) in methanol (15 mL) was added K₂CO₃ (400 mg, 2.89 mmol). After 2.5 h, saturated NH₄Cl was added (35 mL), the mixture was extracted with ethyl acetate (3×40 mL), dried (MgSO₄), filtered, concentrated, and chromatographed on a 16 cm tall×41 mm diameter silica gel column eluting first with 3:2 ethyl acetate:hexane and then with ethyl acetate to afford 31 (600 mg, 66%).

D. [3aR,4R(E),5R,6aS]-5-(t-Butyldiphenylsiloxy)-4-[4-(3-chlorophenoxy)-3,3-(ethylenedioxy)butenyl]-hexahydro-2H-cyclopenta[b]furan-2-one (32)

To a solution of 31 (590 mg, 1.7 mmol), imidazole (168 mg, 2.47 mmol), and DMAP (50 mg, 0.41 mmol) in CH₂Cl₂ (5 mL) was added t-butyldiphenylsilyl chloride (590 mg, 2.15 mmol). After 1 h, saturated NH₄Cl was added (25 mL), the mixture was extracted with CH₂Cl₂ (3×25 mL), ), dried (MgSO₄), filtered, concentrated, and chromatographed on a 16 cm tall×26 mm diameter silica gel column eluting with 1:1 ethyl acetate:hexane to afford 32 contaminated with some Bu$^t$Ph₂SiOH (1.09 g); the mixture was used in the next step without any further purification.

E. [3aR,4R(E),5R,6aS]-5-(t-Butyldiphenylsiloxy)-4-[4-(3-chlorophenoxy)-3,3-(ethylenedioxy)butenyl]-]hexahydro-2H-cyclopenta[b]furan-2-ol (33)

To the above 32: Bu$^t$Ph₂SiOH mixture (1.09 g) in toluene (5.5 mL) at −78° C. (bath temperature) was added DIBAL-H (1.6 mL of a 1.5 M solution in toluene, 2.4 mmol). After 2 h, methanol (3 mL) and ethyl acetate (3 mL) were added, the solution was warmed to room temperature, saturated sodium potassium tartrate (20 mL) was added, and the mixture was stirred for 40 min. The solution was extracted with ethyl acetate (2×40 mL), dried (MgSO₄), filtered, concentrated, and chromatographed on a 15 cm tall×26 mm diameter silica gel column eluting with 1:1 ethyl acetate:hexane to afford 33 (915 mg, 92% from 31).

F. (5Z,13)-(9S,11R)-11-(t-Butyldiphenylsiloxy)-15,15-(ethylenedioxy)-9-hydroxy-16-phenoxy-17,18,19,20-tetranor-5,13-prostadienoic acid isopropyl ester (34)

To a suspension of (4-carboxybutyl)triphenylphosphonium bromide (2.26 g, 5.1 mmol) in THF (10 mL) at 0° C. (bath temperature) was added a 1 M solution of potassium t-butoxide in THF (12 mL, 12 mmol). After 30 min, lactol 33 was added (910 mg, 1.5 mmol) as a solution in THF (10 mL). After an additional 35, min saturated NH₄Cl was added (35 mL), the solution was extracted with ethyl acetate (3×35 mL), dried (MgSO₄), filtered, and concentrated to afford an oil. The oil was dissolved in acetone (15 mL), cooled to 0° C.(bath temperature), and DBU was added (1.2 g, 7.9 mmol). After 25 min, isopropyl iodide was added (1.3 g, 7.8 mmol) and the reaction was warmed to room temperature. After stirring overnight, the solution was added to saturated NH₄Cl (25 mL), extracted with ethyl acetate (3×30 mL), dried (MgSO₄), filtered, concentrated, and chromatographed on a 17 cm tall×26 mm diameter silica gel column eluting with 40% ethyl acetate in hexane to afford 34 as a chromatographically separable mixture with the siloxy transpositional isomer 34* (913 mg total, 83%).

G. (5Z,13E)-(9S,11R)-9,11-Dihydroxy-15,15-ethylenedioxy)-16-phenoxy-17,18,19,20-tetranor-5,13-prostadienoic acid isopropyl ester (VI)

To a solution of a mixture of 34 and 34* (510 mg, 0.72 mmol) in THF (6 mL) was added a 1 M solution of TBAF in THF (1.7 mL, 1.7 mmol). After 2 h, saturated NH₄Cl was added (20 mL), the solution was extracted with ethyl acetate (3×30 mL), dried (MgSO₄), filtered, concentrated, and chromatographed on a 15 cm tall×41 mm diameter silica gel column eluting with ethyl acetate to afford VI (194 mg, 57%). ¹³C NMR (CDCl₃) δ173.67 (C), 158.75 (C), 134.45 (CH), 129.77 (CH), 129.36 (CH), 128.96 (CH), 128.35 (CH), 121.06 (CH), 114.80 (CH), 106.79 (C), 78.22 (CH), 73.28 (CH), 71.26 (CH₂), 67.60 (CH), 65.30 (CH₂), 65.26 (CH₂),55.70 (CH), 50.69 (CH), 42.86 (CH₂), 34.02 (CH₂), 26.60 (CH₂), 25.81 (CH₂), 24.85 (CH₂), 21.83 (CH₃). MS, m/z calcd. for C₂₇H₃₈O₇Na [(M+Na)⁺], 497; found 497.

EXAMPLE 6

Synthesis of VII

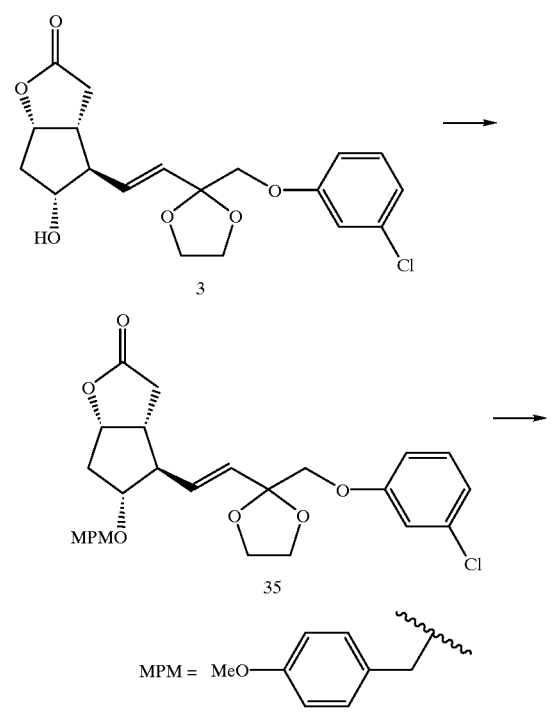

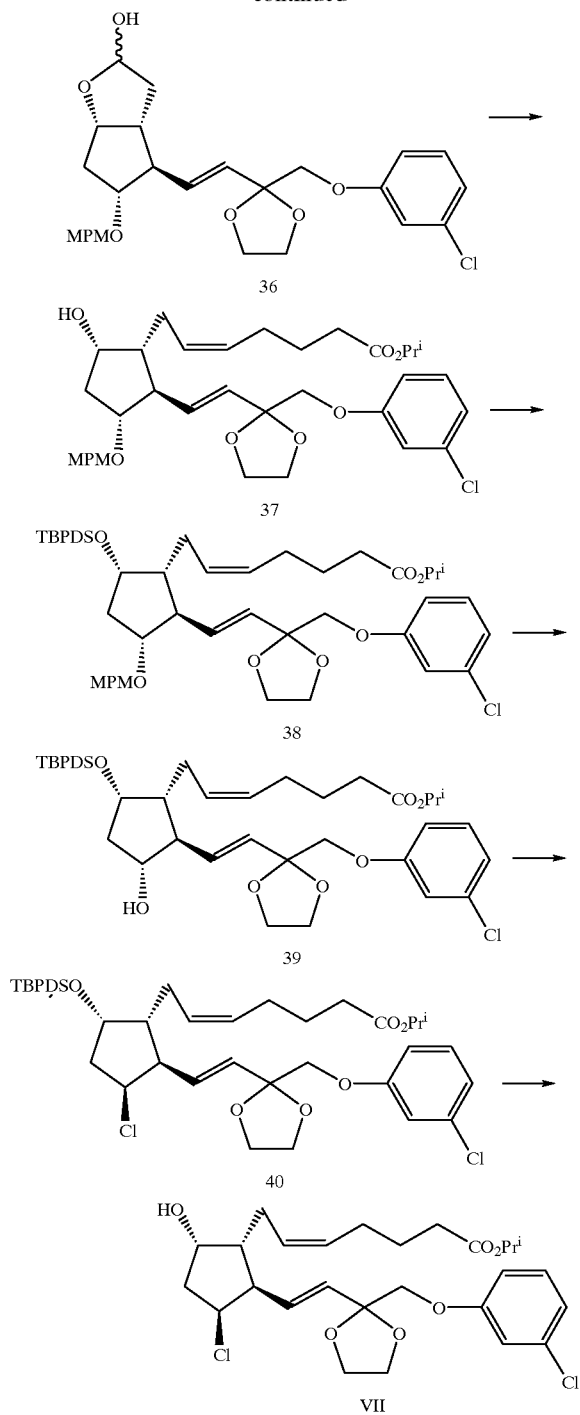

(5Z,13E)-(9S,11S)-1-Chloro-16-(3-chlorophenoxy)-15,15-(ethylenedioxy)-9-hydroxy-17,18,19,20-tetranor-5,13-prostadienoic acid isopropyl ester (VII)

Treatment of alcohol 3 (see Example 1) with 4-methoxybenzyl chloride, (i-C$_3$H$_7$)$_2$NCH$_2$CH$_3$, and Bu$_4$N$^+$ I$^-$ in CH$_2$Cl$_2$ affords lactone 35, which is reduced to by DIBAL in toluene at −78 °C. Wittig olefination with Ph$_3$P$^+$(CH$_2$)$_4$CO$_2$H Br$^-$ in THF in the presence of t-BuOK, followed by esterification of the resultant carboxylic acid with DBU/isopropyl iodide in acetone gives 37. Silylation of the alcohol is effected using t-butyldiphenylsilyl chloride/imidazole in DMF to afford the silyl ether, 38, which is converted to alcohol 39 by DDQ in CH$_2$Cl$_2$/water. Treatment of 39 with CH$_3$SO$_2$Cl and NEt$_3$ in CH$_2$Cl$_2$, followed by heating with Bu$_4$NCl in toluene, yields chloride 40. Deprotection of 40 with TBAF in THF affords VII.

The 15-ketal substituted prostaglandins of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical administration to the patient's eyes.

In forming compositions for topical administration, the compounds of the present invention are generally formulated as between about 0.00003 to about 0.5 percent by weight (wt %) solutions in water at a pH between about 4.5 to about 8.0, preferably between about 7.0 and about 7.5. The compounds are preferably formulated as between about 0.0005 to about 0.03 wt % and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil) cyclodextrin; or other agents known to those skilled in the art. Such co-solvents are typically employed at a level between about 0.01% and about 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of 15-ketal prostaglandins of the present invention include the following Examples 7–10:

EXAMPLE 7

| Ingredient | Amount (wt %) |
| --- | --- |
| Compound III | 0.001 |
| Phosphate Buffered Saline | 1.0 |
| Polysorbate 80 | 0.5 |
| Purified water | q.s. to 100% |

EXAMPLE 8

| Ingredient | Amount (wt %) |
| --- | --- |
| Compound II | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| CREMOPHOR ® EL | 0.1 |
| Benzalkonium chloride | 0.01 |
| HCl and/or NaOH | pH 7.3–7.4 |
| Purified water | q.s. to 100% |

EXAMPLE 9

| Ingredient | Amount (wt %) |
| --- | --- |
| Compound IV | 0.01 |
| Phosphate Buffered Saline | 1.0 |
| Hydroxypropyl-β-cyclodextrin | 4.0 |
| Purified water | q.s. to 100% |

EXAMPLE 10

| Ingredient | Amount (wt %) |
| --- | --- |
| Compound VI or VII | 0.01 |
| CREMOPHOR ® EL | 0.5 |
| Tromethamine | 0.12 |
| Boric Acid | 0.3 |
| Mannitol | 4.6 |
| Disodium EDTA | 0.01 |
| Benzalkonium Chloride | 0.01 |
| NaOH and/or HCl | q.s. to pH 7 |
| Purified water | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma or ocular hypertension in a patient suffering therfrom, which comprises administering to the patient a pharmaceutically effective amount of a compound of formula I:

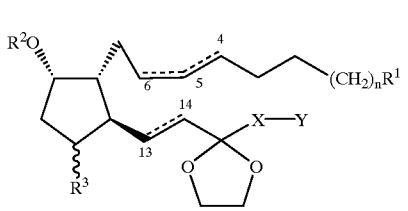

wherein:

$R^1$=$CO_2R$, $CONR^4R^5$, $CH_2OR^6$, or $CH_2NR^7R^8$; where:
R=H or cationic salt moiety, or $CO_2R$=ophthalmically acceptable ester moiety; $R^4$, $R^5$=same or different=H or alkyl; $R^6$=H, acyl, or alkyl; $R^7$, $R^8$=same or different=H, acyl, or alkyl; with the proviso that if one of $R^7$, $R^8$=acyl, then the other=H or alkyl;

n=0 or 2

$R^2$=H, alkyl, or acyl;

$R^3$=H, halo, or $OR^9$; where $R^9$=H, alkyl, or acyl;

- - - - =single or non-cumulated double bond, with the provisos that if a double bond is present between carbons 4 and 5, it is of the cis configuration; and that if a double bond is present between carbons 13 and 14, it is of the trans configuration;

$X$=$(CH_2)_m$ or $(CH_2)_mO$, where m=1–6; and

Y=phenyl, optionally substituted with alkyl, halo, trihalomethyl, alkoxy, acyl, acyloxy, amino, alkylamino, acylamino, or hydroxy; or X—Y=$(CH_2)_pY^1$; where p=0–6; and

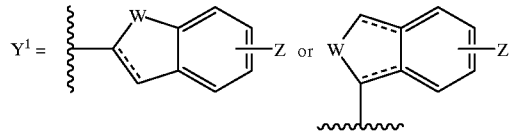

wherein:

W=$CH_2$, O, $S(O)_q$, $NR^{10}$, $CH_2CH_2$, CH=CH, $CH_2O$, $CH_2S(O)_q$, CH=N, or $CH_2NR^9$; where q=0–2, and $R^{10}$=H, alkyl, or acyl;

Z=H, alkyl, alkoxy, acyl, acyloxy, halo, trihalomethyl, amino, alkylamino, acylamino, or hydroxy; and

- - - - =single or double bond;

with the proviso that the following compounds are excluded: etiproston and its pharmaceutically acceptable salts and esters.

2. The method of claim 1, wherein the compound is administered topically.

3. The method of claim 2, wherein the compound is administered as a solution, suspension or emulsion.

4. The method of claim 1, wherein:

$R^1$=$CO_2R$, where R=H; or $CO_2R$=ophthalmically acceptable ester moiety;

$R^2$=H;

n=0;

$R^3$=OH in the alpha (α) configuration, or Cl or F in the beta (β) configuration;

- - - - =single or non-cumulated double bond, with the provisos that if double bond is present between carbons 4 and 5 or carbons 5 and 6, it is of the cis configuration; and that if a double bond is present between carbons 13 and 14, it is of the trans configuration;

X=$CH_2O$; and

Y=phenyl, optionally substituted with halo or trihalomethyl.

5. The method of claim 2, wherein the concentration of the compound is between about 0.00003 to about 0.5 weight percent.

6. The method of claim 5, wherein the concentration of the compound is between about 0.0005 to about 0.03 weight percent.

7. The method of claim 6, wherein the concentration of the compound is between about 0.001 to about 0.01 weight percent.

8. The method of claim 5, wherein the compound is:

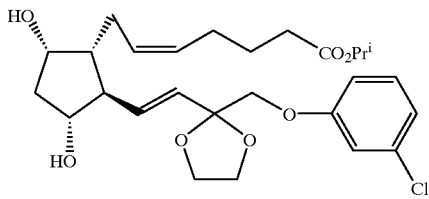

9. The method of claim 5, wherein the compound is:

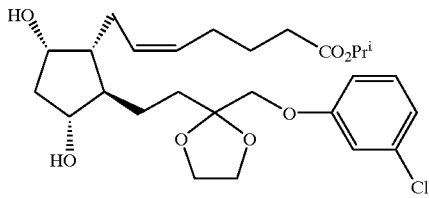

10. The method of claim 5, wherein the compound is:

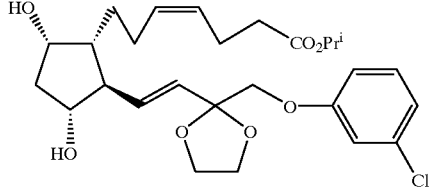

11. The method of claim 5, wherein the compound is:

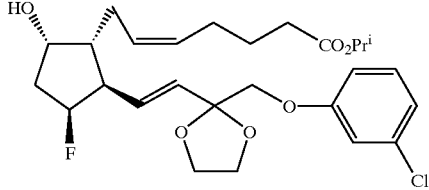

12. The method of claim 5, wherein the compound is:

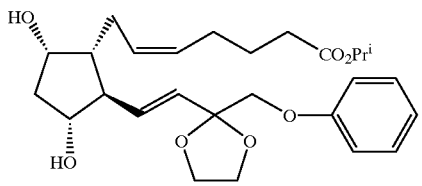

13. The method of claim 5, wherein the compound is:

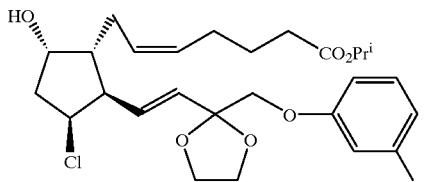

14. A compound of formula (I):

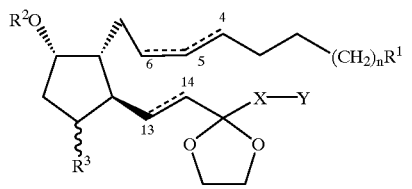

I wherein:

$R^1$=$CO_2R$, $CONR^4R_5$, $CH_2OR^6$, or $CH_2NR^7R^8$; where:
R=H or cationic salt moiety, or $CO_2R$= pharmaceutically acceptable ester moiety; $R^4$, $R^5$=same or different=H or alkyl; $R^6$=H, acyl, or alkyl; $R^7$, $R^8$=same or different=H, acyl, or alkyl; with the proviso that if one of $R^7$, $R^8$=acyl, then the other=H or alkyl;

n=0 or 2;

$R^2$=H, alkyl, or acyl;

$R^3$=H, halo, or $OR^9$; where $R^9$=H, alkyl, or acyl;

[- - -] ===== = single or non-cumulated double bond, with the provisos that a cis double bond is present between carbons 4 and 5; and that if a double bond is present between carbons 13 and 14, it is of the trans configuration;

X=$(CH_2)_m$ or $(CH_2)_mO$, where m=1–6; and

Y=phenyl, optionally substituted with alkyl, halo, trihalomethyl, alkoxy, acyl, acyloxy, amino, alkylamino, acylamino, or hydroxy; or X—Y=$(CH_2)_pY^1$; where p=0–6; and

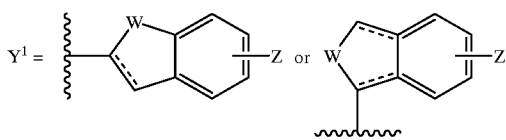

wherein:
W=$CH_2$, O, $S(O)_q$, $NR^{10}$, $CH_2CH_2$, CH=CH, $CH_2O$, $CH_2S(O)_q$, CH=N, or $CH_2NR^9$, where q=0–2, and $R^{10}$=H, alkyl, or acyl;
Z=H, alkyl, alkoxy, acyl, acyloxy, halo, trihalomethyl, amino, alkylamino, acylamino, or hydroxy; and

[----] ==== = single or double bond.

15. The compound of claims 14 wherein:
$R^1$=$CO_2R$; where R=H; or $CO_2R$=pharmaceutically acceptable ester moiety, where R=alkyl;
n=0;
$R^2$=H;
$R^3$=OH in the alpha (α) configuration, or Cl or F in the beta (β) configuration;
X=$CH_2O$; and
Y=phenyl, optionally substituted with halo or trihalomethyl.

16. The compound of claim 15, having the formula:

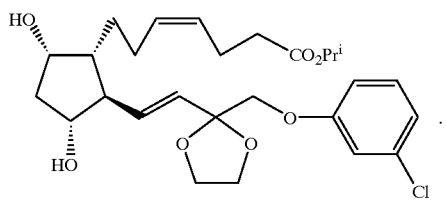

17. An ophthalmic composition for the treatment of glaucoma and ocular hypertension, comprising a compound of formula I:

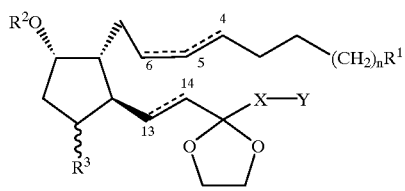

wherein:
$R^1$=$CO_2R$, $CONR^4R^5$, $CH_2OR^6$, or $CH_2NR^7R^8$; where:
R=H or cationic salt moiety, or $CO_2R$=ophthalmically acceptable ester moiety; $R^4$, $R^5$=same or different=H or alkyl; $R^6$=H, acyl, or alkyl; $R^7$, $R^8$=same or different=H, acyl, or alkyl; with the proviso that if one of $R^7$, $R^8$=acyl, then the other=H or alkyl;

n=0 or 2
$R^2$=H, alkyl, or acyl;
$R^3$=H, halo, or $OR^9$; where $R^9$=H, alkyl, or acyl;
----=single or non-cumulated double bond, with the provisos that [if a double bond] a cis double bond is present between carbons 4 and 5, and that if a double bond is present between carbons 13 and 14, it is of the trans configuration;
X=$(CH_2)_m$ or $(CH_2)_mO$, where m=1–6; and
Y=phenyl, optionally substituted with alkyl, halo, trihalomethyl, alkoxy, acyl, acyloxy, amino, alkylamino, acylamino, or hydroxy; or
X—Y=$(CH_2)_pY^1$; where p=0–6; and

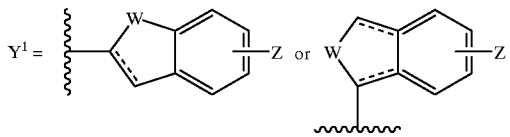

wherein:
W=$CH_2$, O, $S(O)_q$, $NR^{10}$, $CH_2CH_2$, CH=CH, $CH_2O$, $CH_2S(O)_q$, CH=N, or $CH_2NR^9$, where q=0–2, and $R^{10}$=H, alkyl, or acyl;
Z=H, alkyl, alkoxy, acyl, acyloxy, halo, trihalomethyl, amino, alkylamino, acylamino, or hydroxy; and
----=single or double bond;
and an ophthalmically acceptable vehicle therefor.

18. The composition of claim 17 wherein:
$R^1$=$CO_2R$; where R=H; or $CO_2R$=ophthalmically acceptable ester moiety, where R=alkyl;
n=0;
$R^2$=H;
$R^3$=OH in the alpha (α) configuration, or Cl or F in the beta (β) configuration;
X=$CH_2O$; and
Y=phenyl, optionally substituted with halo or trihalomethyl.

19. The composition of claim 18, wherein the compound is of the following formula:

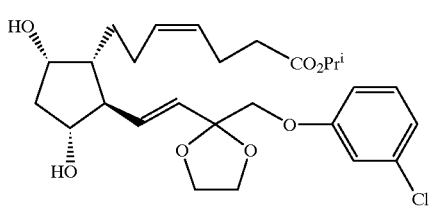

20. A method of treating glaucoma or ocular hypertension in a patient, which comprises administering to the patient a pharmaceutically effective amount of a composition consisting essentially of isopropyl ester of etiproston and a pharmaceutically acceptable vehicle therefor.

* * * * *